United States Patent [19]

Gray et al.

[11] Patent Number: 5,630,434
[45] Date of Patent: *May 20, 1997

[54] FILTER REGENERATION SYSTEM

[76] Inventors: Donald J. Gray, 9 McGraw Ct., East Greenwich, R.I. 02818; Peter T. E. Gebhard, III, 335 Valley St., Providence, R.I. 02908

[*] Notice: The term of this patent shall not extend beyond the expiration date of Pat. No. 5,240,507.

[21] Appl. No.: 467,357

[22] Filed: Jun. 6, 1995

Related U.S. Application Data

[63] Continuation-in-part of Ser. No. 281,303, Jul. 27, 1994, Pat. No. 5,538,025, which is a continuation-in-part of Ser. No. 53,161, Apr. 26, 1993, Pat. No. 5,469,876, which is a continuation of Ser. No. 787,935, Nov. 5, 1991, Pat. No. 5,240,507.

[51] Int. Cl.⁶ ............................ B08B 3/10; B08B 5/04
[52] U.S. Cl. ......................... 134/10; 134/19; 134/21; 134/22.15; 134/11
[58] Field of Search .............................. 134/21, 11, 10, 134/22.15, 19

[56] References Cited

U.S. PATENT DOCUMENTS

| | | | |
|---|---|---|---|
| 3,610,260 | 10/1971 | Kearney | 134/12 |
| 4,023,984 | 5/1977 | Clementson et al. | 134/38 |
| 4,141,373 | 2/1979 | Kartanson et al. | 134/21 |
| 4,303,454 | 12/1981 | Petterson et al. | 134/11 |
| 4,424,633 | 1/1984 | Bernhardt et al. | 34/75 |
| 4,513,590 | 4/1985 | Fine | 68/18 |
| 4,601,181 | 7/1986 | Privat | 68/18 |
| 4,865,061 | 9/1989 | Fowler et al. | 134/108 |
| 4,879,004 | 11/1989 | Oesch et al. | 203/89 |
| 4,879,888 | 11/1989 | Suissa | 68/18 |
| 4,912,793 | 4/1990 | Hagiwara | 8/158 |
| 4,931,104 | 6/1990 | Burke | 134/40 |
| 4,980,017 | 12/1990 | Kaji et al. | 156/642 |
| 4,984,318 | 1/1991 | Coindreau-Palau | 8/158 |
| 5,045,117 | 9/1991 | Witherell | 134/21 |
| 5,051,135 | 9/1991 | Tanaka et al. | 134/10 |
| 5,056,174 | 10/1991 | Hagiwara | 8/158 |
| 5,106,404 | 4/1992 | Grant | 55/195 |
| 5,115,576 | 5/1992 | Roberson, Jr. et al. | 34/15 |
| 5,240,507 | 8/1993 | Gray et al. | 134/21 |
| 5,246,501 | 9/1993 | Rodgers et al. | 134/10 |
| 5,314,509 | 5/1994 | Kato et al. | 34/406 |

FOREIGN PATENT DOCUMENTS

| | | |
|---|---|---|
| 0381887A1 | 8/1990 | European Pat. Off. . |
| 0563380A1 | 10/1993 | European Pat. Off. . |
| 1143923 | 10/1957 | France . |
| 1338398 | 1/1964 | France . |
| 88834 | 6/1967 | France . |
| 55-17389 | 9/1981 | Japan . |
| 1135181 | 12/1968 | United Kingdom . |
| WO93/10302 | 5/1993 | WIPO . |

OTHER PUBLICATIONS

Purported English language translation of item AL, above.
Abstract of Japan for Jp403234021 dated Oct. 1991 by Masaya Kabasawa.

*Primary Examiner*—Zeinab El-Arini
*Attorney, Agent, or Firm*—Foley, Hoag & Eliot LLP

[57] ABSTRACT

Stripping contaminants/impurities from a filter includes subjecting the filter to a negative gauge pressure and applying superheated solvent vapor to the filter while maintaining the negative gauge pressure. The filter can be heated prior to being subjected to the negative gauge pressure. The superheated vapor may be composed of the same compounds as impurities being removed from the filter. The filter may be an activated carbon filter.

6 Claims, 3 Drawing Sheets

FILTER REGENERATION SYSTEM

This application is a continuation-in-part of U.S. patent application Ser. No. 08/281,303 filed Jul. 27, 1994 and now U.S. Pat. No. 5,538,025 which is a continuation-in-part of U.S. patent application Ser. No. 08/053,161 filed Apr. 26, 1993 and now issued as U.S. Pat. No. 5,469,876 which is a division of U.S. patent application Ser. No. 07/787,935 filed Nov. 5, 1991 and now issued as U.S. Pat. No. 5,240,507.

TECHNICAL FIELD

This invention relates to an improved cleaning system, and more particularly to a closed solvent cleaning method and system which eliminates mixture of the solvent with air throughout the cleaning operation.

BACKGROUND OF THE INVENTION

Cleaning operations are becoming more of a burden on industry because of increasing strictness in environmental regulations relating to disposition of compounds emitted as a result of cleaning operations. The cleaning operations affected include the cleaning of clothing, rugs, and furnishings as well as industrial cleaning applications where solvent is used to degrease metals, ceramics, plastics, and other materials.

There are two types of solvent cleaning processes: open and closed. Open systems include solvent vapor degreasing, solvent ultrasonic cleaning, cold or hot solvent dipping and solvent spraying systems. Open solvent cleaning systems contaminate the environment and are relatively costly to operate due to the cost of constantly replenishing non-recoverable solvent. Also, add-on equipment to contain solvent vapor and to properly dispose of solvent vapor and liquid waste is also costly.

Closed solvent cleaning systems attempt to address the problems of open systems by maintaining an airtight seal in the cleaning chamber while solvent is being applied to the parts that are being cleaned. However, solvent is still lost in closed systems. Although the system is closed when the solvent is introduced into the cleaning chamber, the solvent still mixes with air inside the cleaning chamber. After the cleaning operation, the liquid solvent can be easily separated from the air, but the vapor solvent is more difficult to remove, even if the vapor solvent is first condensed. The vapor escapes when the cleaned parts are removed because the cleaned parts include solvent which remains on the surfaces and in the pores of the parts. Attempts to recover this solvent are expensive and less than totally successful.

Another technique for eliminating potentially contaminating solvent is incineration. However, incineration requires significant investment in special equipment, uses extra heat energy, and destroys solvent that must then be replenished for subsequent cleaning cycles. Steam stripping, another solvent elimination technique, recovers the solvent but requires special equipment and heat energy to make the steam. Also, steam stripping requires that the steam be condensed to water and then separated from the solvent, which requires additional energy input to the system.

Conventional cleaning systems have other problems in the area of hazardous emissions and solvent recovery. They are generally limited to operating at specific temperatures and pressures. They typically do not dry all the solvent off the objects before exposing them to the atmosphere. They utilize heat energy during a substantial part, if not all, of the cleaning cycle. Conventional systems also need a great deal of solvent to fill their cleaning tanks and require additional energy input to pump the solvent through the system. In addition, some solvent vapor cleaning systems must use solvents whose vapors are heavier than air. These vapors are maintained in a blanket over the boiling solvent by using expensive refrigerator coils and by limiting the dimensions of the system tank. These systems operate at fixed temperatures which are determined by the boiling point of the solvent at atmospheric pressure.

A different approach, known as vacuum degreasing, avoids some of the difficulties associated with solvent cleaning. In this approach, the contaminants are exposed to a high temperature, low-pressure environment in order to reach pressures below the vapor pressure of the contaminant. Essentially the contaminant is boiled off the parts. However, some contaminants have a very low vapor pressure and consequently require extremely high vacuums and/or temperatures for vacuum degreasing. Furthermore, although solvents are not used, the contaminants from the part may be pollutants and therefore cannot be released to the environment. Also, vacuum degreasing can be costly due to the subtorr pressures and high temperatures required. In many cases, non-volatile residue, either present in the contaminant originally (i.e., sulfur residue) or residue resulting from a breakdown of the contaminant due to the high temperature requirements (e.g. carbon deposits) are often left behind on the parts. The pollution abatement energy costs and cleaning efficiency requirements strongly limit the applications of such systems.

Furthermore, often filters are used to remove contaminants from gasses being emitted by solvent cleaning systems. The filters can use a material such as activated carbon to absorb the contaminants. However, once these filters become saturated, they must be purged of contaminants prior to further use. Methods of purging include air or steam stripping, both of which result in transferring the contaminants to the steam or the air, respectively, thus requiring the steam or the air to then also be purged of contaminants at additional cost.

SUMMARY OF THE INVENTION

According to the present invention, a closed-circuit solvent cleaning operation includes evacuating a cleaning chamber containing parts to be cleaned before solvent is introduced, providing solvent to the chamber to clean the parts, and recovering the solvent by extracting and condensing the solvent prior to the exposure of the chamber and parts to the atmosphere during removal of parts from the chamber after the cleaning operation has been completed. The recovered solvent can be cleaned for reuse in a subsequent operation.

A negative gauge pressure in the chamber may be in the range of atmospheric to zero atmospheric absolute. The solvent may be introduced in a vapor state, a liquid state, or both. The temperature of the chamber may be varied to control the temperature and vapor density of the solvent in order to increase or decrease the penetration of the solvent into the object to be cleaned and to create more or less pressure that can be used to drive the solvent through the closed system. Recovering the solvent may include draining liquid solvent and any contaminant contained therein from the chamber and then drawing off vapor solvent from the chamber. Draining the liquid solvent may include maintaining the chamber at an elevated temperature to generate increased pressure in the chamber to drive the liquid solvent out of the chamber. Drawing the vapor solvent may include drying the solvent off the object.

An apparatus for performing the operations discussed above includes a closed solvent cleaning system with a chamber for holding an object to be cleaned and means for applying a negative gauge pressure to the chamber to remove air and other non-condensible gases. Also included is means for introducing solvent to the chamber and means for recovering the solvent from the object and chamber. Storage means may store the recovered solvent.

In a preferred embodiment, the chamber may include a heat exchanger for varying the temperature of the chamber. The means for applying a negative gauge pressure may include a vacuum pump and the means for introducing the solvent may include a valve in communication with the storage means. The means for recovering may include a drain for extracting the solvent liquid and contaminants and may include means for extracting the solvent vapor as well. The storage means may include one reservoir for receiving the solvent vapor and a second reservoir for receiving the solvent liquid, and the system may include means for condensing the solvent vapor.

The system may also include means for spraying solvent over the parts to be cleaned, for immersing the parts in solvent, or both. In addition, there may be means for throttling solvent vapors into the chamber to assist in drying. Means for processing and cleaning contaminated solvent within the closed circuit includes a distilling tank and a holding tank and means for heating the distillation tank, distilling solvent vapor and urging the distilled vapor into the holding tank.

The chamber may be evacuated by employing a negative pressure which generally is less than the vapor pressure at the operating temperature of the solvent and the contaminants to be removed such as water vapor and non-condensible gases. Subtorr levels are not generally required. Torr levels of zero to seven hundred torr are operable with levels between one and fifty being workable and levels at or near one torr being preferred. Since air is evacuated from the system prior to introducing the solvent and the solvent is removed prior to reintroducing the air, the atmosphere is not contaminated and the solvent may be recovered easily without the necessity to separate the solvent from air.

A valve may be opened to permit solvent to flow or to flash in vapor form from the higher pressure holding tank to the lower pressure chamber without requiring pumping equipment and the associated added energy expense thereof. Alternatively, the liquid solvent may be drained by gravity. Because of the control afforded by the closed operation of the invention, the solvent can be heated or cooled and/or the pressure can be increased or decreased to whatever levels are desirable for a particular cleaning task. For example, the pressure in the chamber can be increased to above atmospheric to enhance cleaning efficiency or the temperature could be increased above the ambient temperature. Prior to the object being removed or any venting to atmosphere, the solvent may be returned to the storage tank and recovered. The liquid may be recovered first, as it typically will reside at the bottom of the tank and contain the contaminants that have been removed from the clean part. The system may throttle solvent vapors about the parts to be cleaned, thereby aiding in drying the parts after cleaning. The system may also clean contaminated solvent within the closed circuit. The system may also separately recover liquid and vapor solvent since the recovered vapor is relatively free of contaminants compared to the liquid. The vapor may be condensed in its travel back to the holding tank. The vapor removal from the chamber can be sufficiently thorough so that drying of the parts occurs.

A heat exchanger or similar device may be provided with the chamber in order to control the temperature of the cleaning process. Thus, certain materials which cannot withstand elevated temperatures or perhaps even room temperatures during the cleaning process may be accommodated by simply cooling the chamber. The heat exchanger may also increase the temperature in the chamber to accomplish a number of different goals. Increased temperature increases the penetration of the vapor into the part to be cleaned and thus enhances the cleaning function. Increased temperature also increases the chemical and physical cleaning characteristics of the solvent and thus enhances the cleaning function. Increased temperature also increases the vapor pressure in the chamber which can be used to drive out the liquid and vapor solvents. The heating or cooling that is applied to the chamber may be applied only during the cleaning cycle at a great saving of energy over those systems that apply heat during the entire cleaning operation.

According further to the present invention, clothes are dry cleaned by placing the clothes in a tumbler/dryer, sealing the tumbler/dryer, applying a negative gauge pressure to the tumbler/dryer, providing solvent to the tumbler/dryer, activating the tumbler/dryer to dry clean the clothes, removing the solvent from the tumbler/dryer, and simultaneously throttling hot solvent vapor into the tumbler/dryer while removing vapor from the tumbler/dryer in order to dry the clothes. The solvent may be perchloroethylene, trichloroethylene, stodard solvent, fluorinated ethers, alcohols, or other flammable solvents. The negative gauge pressure in the tumbler/dryer can be maintained via a pump which removes vapor from the tumbler/dryer. The solvent can be heated prior to introduction into the tumbler/dryer.

According further to the present invention, stripping contaminants/impurities from a filter includes subjecting the filter to a negative gauge pressure and applying superheated solvent vapor to the filter while maintaining the negative gauge pressure. The filter can be heated prior to being subjected to the negative gauge pressure. The superheated vapor may be composed of the same compounds as impurities being removed from the filter. The filter may be an activated carbon filter.

The invention provides an efficient, economical, safe, and environmentally sound solvent cleaning technique that eliminates the need of having to separate the solvent from air after the cleaning operation.

One of the advantages of such a system is that it can work with solvents in the vapor form, in the liquid form or both, and it can work with a variety of different solvents such as 1.1.1. trichloroethane, trichloroethylene, methylene chloride, perchloroethylene, Freon, aldehydes, alcohols, amines, ketones, aromatics, or other solvents which may or may not be heavier than air. Another feature of the system according to this invention is that it overcomes the problem of solvent and/or liquid penetrating small areas such as tapped holes in the parts to be cleaned since the air is removed before solvent is introduced.

The system enables efficient solvent recovery, which is increasingly important as solvent prices increase and as allowable solvent emissions decrease. The invention uses much less solvent than prior art systems since the vapor is flashed into the cleaning chamber so that the entire cleaning chamber or tank does not have to be filled with liquid solvent. Also, initial evacuation of the chamber after the parts are inserted for cleaning removes volatile contaminants that may be associated with the parts before the solvent is introduced.

The system cleans more efficiently by condensing vapor on parts to cause a vapor wash and cleaning. The system is much more efficient because heat is required for much less of the time during the cycle.

In the case of the dry cleaning system, relatively little solvent remains on the clothes or is emitted from the system, thus allowing the use of solvents which would otherwise be environmentally unacceptable for conventional dry cleaning systems. Also, since most of the solvent is recovered during the cleaning operation, less solvent is required to operate the system. Also, much less energy is used since, unlike prior art dry cleaning systems, there is no need to remove solvent vapor from air using energy to cool the air.

For the filter regeneration system, the contaminants are removed from the filter without air or steam stripping, thus eliminating the need to subsequently remove the contaminants from the steam or air. Furthermore, when the filter is part of a closed circuit cleaning system, contaminants can be removed from the filter using components of the closed circuit system, thus facilitating removal without additional handling or off-line processing of the filter.

BRIEF DESCRIPTION OF DRAWINGS

Other objects, features and advantages will occur to those skilled in the art from the following description of a preferred embodiment and the accompanying drawings, in which:

FIG. 4 is a flow chart depiction operation of the filter regeneration system shown in FIG. 3.

DETAILED DESCRIPTION OF THE PREFERRED EMBODIMENTS

Figure 1:
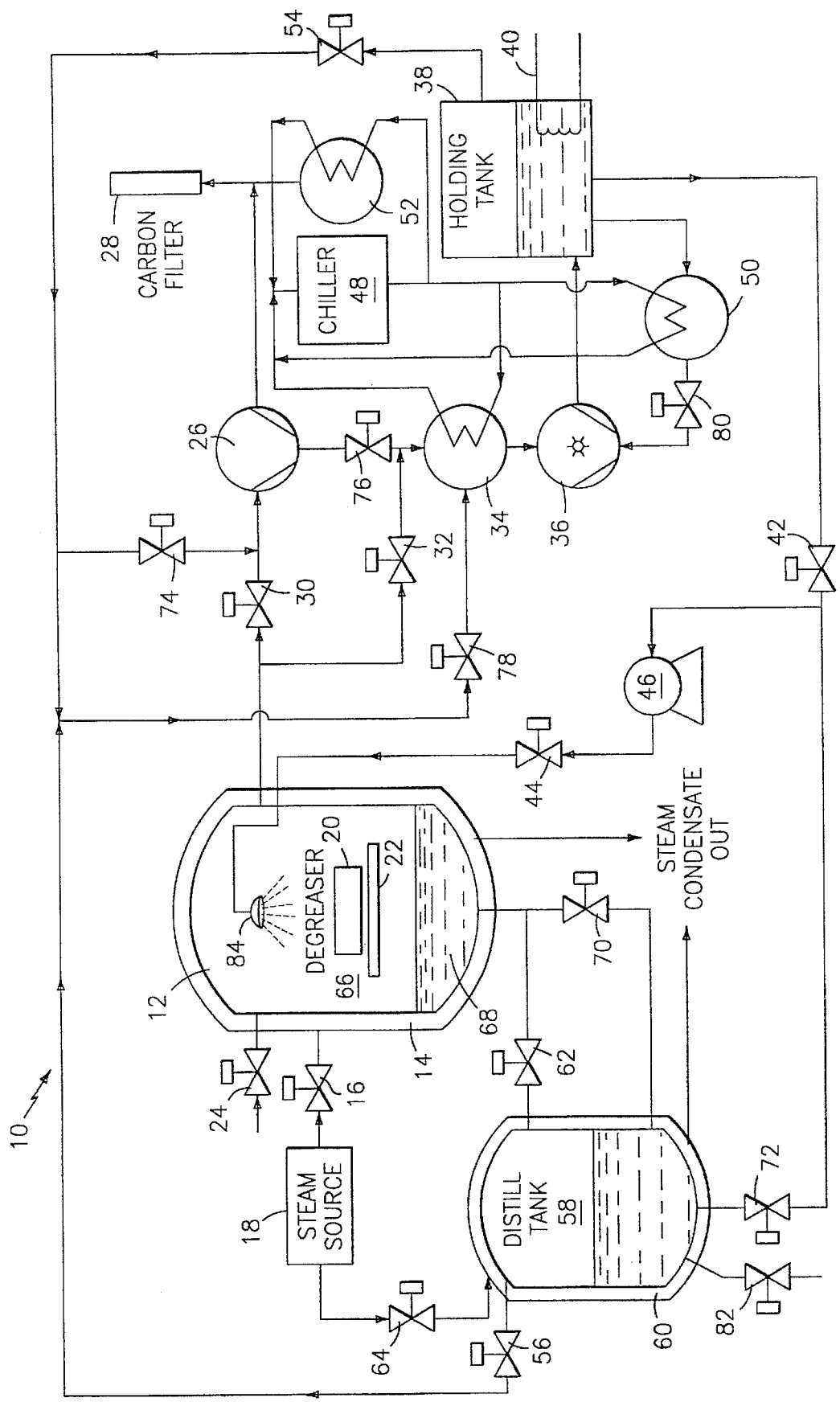
FIG. 1 is a schematic diagram of a closed circuit solvent cleaning system according to this invention.

Referring to FIG. 1, a system 10 includes a cleaning or degreasing tank or chamber 12 having a heat exchanger 14. A valve 16 controls inlet flow of heating or cooling fluid into the heat exchanger 14. In the embodiment illustrated herein, the heat exchanger 14 is provided with a heating fluid obtained from a steam source 18. The chamber 12 can be heated in a variety of other conventional manners, not illustrated herein, including by electrical heaters or by using other heat transfer liquids such as oil.

A part to be cleaned 20 is placed on a suitable support 22 within the chamber 12. A valve 24, which operates to vent the chamber 12 to the atmosphere, is closed. A pump 26, operating as a vacuum pump, applies a negative gauge pressure to the chamber 12. An activated charcoal filter (not shown) may be added to absorb any residual solvent vapors before they enter the vacuum pump 26. A valve 30 vents outflow through the vacuum pump 26 to a carbon filter 28 while a valve 32, during a different portion of the cleaning cycle, directs outflow of the chamber 12 to a condenser/heat exchanger 34 and through the vacuum pump 36 to a holding tank 38 for storing clean solvent. The holding tank 38 is provided with a heater 40 to heat solvent stored therein. The holding tank 38 provides solvent to the chamber 12 through two valves 42, 44 and a pump 46. Note that in some cases the pumps 26, 36, 46 can be replaced with conventional ejectors which use the motive force of gases in the system 10 or compressed air to move other gases through the system 10.

A chiller unit 48 provides coolant to the heat exchanger 34, and to two other heat exchangers 50, 52. Coolant can be provided to the heat exchangers 34, 50, 52 by other conventional means, such as providing cold water directly from a source of cold water or from a cooling tower. The heat exchanger 50 cools solvent stored in the holding tank 38 when a valve 80 is opened to allow solvent to be drawn through the heat exchanger 50 by the pump 36. The heat exchanger 52 cools vapors leaving the holding tank 38 so that solvent in vapor form is liquefied and drips back into the holding tank 38.

A distillation tank 58 for storing solvent from the chamber 12 is in communication both with the chamber 12 and with the holding tank 38. The distillation tank 58 is provided with a heater 60 for heating the solvent therein. The heater 60 is provided with steam from the steam source 18 via a valve 64. Solvent from the distillation tank 58 is provided to the chamber 12 either through a valve 62 or a valve 70.

Two valves 54, 56 are used to purge vapor from the holding tank 38 and the distillation tank 58, respectively. Vapor from one or both of the valves 54, 56, is drawn by the pump 26 through a valve 74 to the carbon filter 28 or a similar filter before the filtered vapor is vented to atmosphere. A third input to the carbon filter 28 may be delivered through the valve 30 which may be interconnected with the chamber 12 so that the outflow from the chamber 12 is drawn by the vacuum pump 26 and filtered through the carbon filter 28 before being vented to atmosphere. This is especially important if there are volatile toxic contaminants associated with the parts that are drawn off by the initial evacuation of chamber 12.

To operate the system 10, the heater 60 is activated to increase the temperature of solvent stored in the distillation tank 58 to 100° C. to produce a 400 torr vapor pressure. The solvent tetrachloroethylene may be used. Heating is accomplished by steam directed from the steam source 18 though the valve 64. Heating can also be accomplished by other conventional means such as electric heaters or heat transfer fluids. The valve 24 is then opened, venting the chamber 12 to atmosphere, the part 20 is placed on the support 22 in the chamber 12, the valve 24 is closed and the vacuum pump 26 is actuated. All of the air, non-condensible gases and any volatile vapor contaminants present are drawn off by the vacuum pump 26 and are directed by opening the valve 30 directly to atmosphere or, alteratively, first through the carbon filter 28, and then to atmosphere. The vacuum pump 26 is then shut off. Since the tetrachloroethylene solvent in the distilling tank 58 is at 100° C., with a 400 torr vapor pressure, then when the valve 62 is opened, solvent vapor flashes into the chamber 12 so that the vapor 66 fills chamber 12 and condenses on and cleans the part 20. If desired, liquid solvent 68 may also be introduced by opening the valve 70 and partially or fully filing the chamber 12 to submerge the part 20 to provide liquid cleaning. If spraying is desired, the valves 44, 42 can be opened and the pump 46 can be activated to draw solvent through the sprayer 84 into the chamber 12. Alternatively, solvent can be provided to the sprayer 84 by opening a valve 71 and the valve 44 and activating the pump 46 to draw solvent from the distilling tank 58. During this process the valves 16, 64 may be opened and the steam source 18 may be activated to increase the temperature of the chamber 12 to approximately 121° C., providing a 760 torr or one atmosphere pressure in the chamber during cleaning. After the cleaning cycle has been completed, the steam source 18 may be shut down and the valves 16, 64 closed. The valve 62 may be periodically opened to allow the liquid solvent 68 to gravity drain back through the open valve 62 to the distilling tank 58. Alternatively, the increased pressure of 760 torr in the chamber 12 can be used to drive the liquid (and any contaminants contained therein after cleaning) back into the distilling tank 58. The pressure in the chamber 12 would then drop to about 400 torr.

Following cleaning, the vapors in the chamber 12 may be drawn off and the part 20 may be dried by activating the heat exchanger 34, opening the valve 32, and the activating the vacuum pump 36. The vapor, being virtually contaminant-free, is condensed in the condenser 34 and provided to the holding tank 38, which stores only clean solvent that can be used when the solvent in the distilling tank 58 becomes contaminated and must be removed via a valve 82 and processed. Vapor is periodically purged from tanks 38, 58 using the valves 54, 56, as described above.

The part 20 can be dried in the chamber 12 by throttling vapor solvent in the tank 58 through the valve 62 while simultaneously maintaining a reduced pressure in the chamber 12 by pulling vapor out of the chamber 12 through a valve 78 and the condenser 34 by the pump 36. The hot vapor solvent heats any liquid that remains on the part 20 which, because of the low pressure in the chamber 12, causes the liquid to change to vapor that leaves the tank via the valve 78.

At the end of the process, the vacuum pump 34 is deactivated, the valve 24 is opened to vent the chamber 12 to atmosphere, and the part 20 is removed. The part 20 is thus dried and cleaned without introducing any hazardous waste to the atmosphere. Also, the solvent is fully recovered with a minimum of effort and expense since the solvent is never mixed with air during the process, thus eliminating the need to undertake expensive and complex procedures required to separate solvent from air to clean the air of solvent contaminants.

Solvent in the distilling tank 58 that has become contaminated can be distilled by opening the valve 64 from steam source 18, and flashing vapors through the valves 56 and 78. The pump 36 pulls vapors through the condenser 34 and sends clean solvent into the holding tank 38. Upon solvent recovery, contaminants can be removed from the distillation tank 58 through the valve 82. Clean solvent can then be returned to the distilling tank 58 through the valves 42, 72 for reuse.

Figure 2:
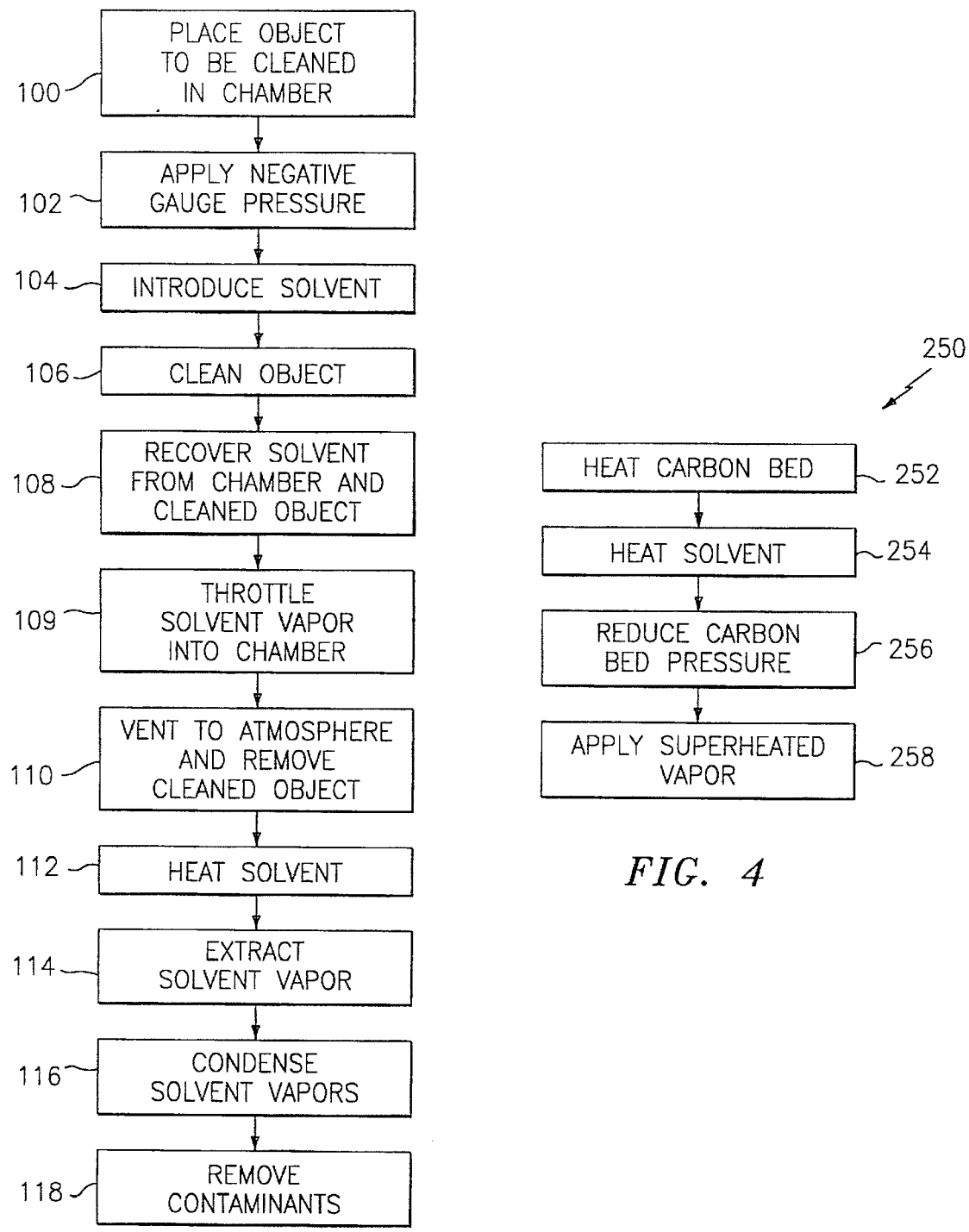
FIG. 2 is a flow chart depicting the operation of the improved closed circuit solvent cleaning system of FIG. 1 according to this invention.

Referring to FIG. 2, a flow chart depicts operation of the system 10 shown in FIG. 1. At a step 100, the object to be cleaned, such as a piece of clothing or a manufactured part, is placed in the cleaning chamber. Following the step 100 is a step 102 where a negative gauge pressure is applied. The step 102 removes air and other non-condensible gases and also removes any volatile contaminants. Optionally, the gasses evacuated from the chamber 12 can be passed through suitable filters. The negative gauge pressure in the chamber 12 may be between atmospheric and zero atmospheric absolute. Pressures in the range of one torr appear to be optimal in certain preferred embodiments.

Following the step 102 is a step 104 where the solvent is introduced. The solvent can be provided in vapor or liquid form, or both. Following the step 104 is a step 106 where the object is cleaned for an appropriate period of time. During the step 106, the temperature can be varied to favor the appropriate conditions for the material or object being cleaned and also to improve vapor density and penetration of the solvent into the object. The temperature increase or decrease can occur only during the cleaning operation so that there is a substantial saving in energy. There can also be a substantial saving in energy because an increased temperature of the chamber 12 increases the differential pressure between the chamber 12 and the distillation tank 58 so that the differential pressure can be used to drive the solvent out of the chamber 12 after the cleaning operation is complete.

Following the step 106 is a step 108 where the solvent is recovered by first removing any solvent liquid, which may contain contaminants, and then removing any solvent vapor which contains virtually no contaminants since the vapor is a distillation product. A complete removal of the vapor at this point also helps to dry the object, thus further minimizing the contamination of the environment with solvents that would ordinarily cling to the object when the cleaning process is complete. Following the step 108 is a step 109 in which the parts 20 are dried by throttling hot solvent vapors thereon in the manner described above. Following the step 109 is a step 110 where the chamber 12 is opened to atmosphere and the cleaned object is removed.

When the solvent in the holding tank 38 becomes contaminated, it is can be distilled. Following the step 110 is a step 112 where the solvent is heated. Following the step 112 is a step 114 where the solvent vapors are extracted. At a step 116, the solvent vapor is condensed and stored in the distillation tank 58. The contaminates can then be removed from the holding tank 38 at a step 118.

Figure 3:
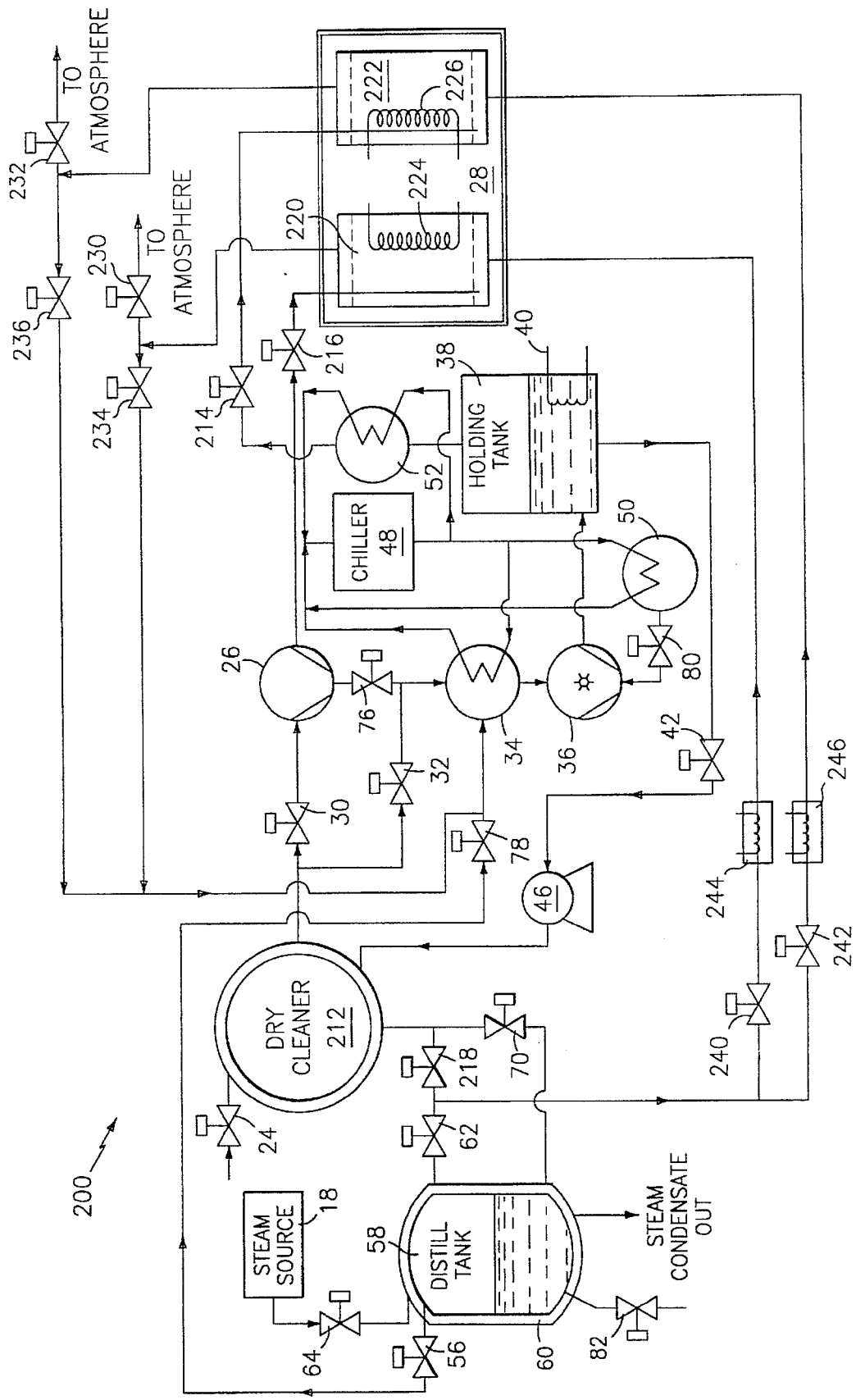
FIG. 3 is a schematic diagram illustrating a dry cleaning system with filter regeneration.

Referring to FIG. 3, a system 200, for dry cleaning clothes is similar to the system 10 shown in FIG. 1. Elements of FIG. 3 having the same reference number as elements in FIG. 1 are analogous and are assumed to have been adequately described in the explanation accompanying FIG. 1. Elements of FIG. 3 that are not found in FIG. 1 are described below.

The chamber 12 shown in FIG. 1 is replaced in FIG. 3 with a conventional tumbler/dryer 212 used for dry cleaning clothes. Unlike the chamber 12 of FIG. 1, the tumbler/dryer 212 is not heated since dry cleaning preferably occurs at room temperature. Accordingly, the tumbler/dryer 2 12 is shown without a heater and without a connection to the steam source 18. In a preferred embodiment, the solvent perchloroethylene is used. Alternatively, the system 200 can instead use other types of solvents such as at least one of: trichloroethylene, stodard solvent, fluorinated ethers, alcohols, and other flammable solvents.

The dry cleaning system 200 does not use a sprayer such as the sprayer 84 shown in FIG. 1. Instead, liquid solvent is provided from the holding tank 38 to the tumbler/dryer 212 via the valve 42 and the pump 46. The perchloroethylene provided to the tumbler/dryer 212 may be at room temperature. Alternatively, the temperature of the perchloroethylene can be raised to slightly higher than room temperature by activating the heating element 40 to heat the solvent stored in the holding tank 38.

Air from the tumbler/dryer 2 12 is provided to the carbon filter 28 via the valve 30, the pump 26, and at least one of two valves 214, 216. Similarly, vapors from the holding tank 38 first pass through the condenser 52 and enter the carbon filter 28 via at least one of the valves 214, 216.

In operation, the tumbler/dryer 212 is purged of air after the clothes to be cleaned are placed therein so that the tumbler/dryer 212 is at a reduced pressure. Air is purged by activating the pump 26, opening the valve 30, and opening at least one of the valves 214, 216. Once the air in the tumbler/dryer 212 has been evacuated, fresh perchloroethylene is provided to the dryer/tumbler 212 via the holding tank 38, the valve 42, and the pump 46. The clothes are dry cleaned by the tumbler/dryer 212 in a conventional manner but at reduced pressure, similar to the cleaning process described in connection with FIGS. 1 and 2. Following cleaning, dirty liquid solvent is drained from the tumbler/dryer 212 to the distillation tank 58 by opening the valve 70. After the solvent has been drained, the clothes are dried without introducing any appreciable solvent vapors to the atmosphere in a manner described in detail below.

In order to dry the clothes, the heater 60 for heating solvent contained in the distillation tank 58 is activated by opening the valve 64 that connects the steam source 18 to the heater 60. Simultaneously, a valve 218 is opened in order to provide hot vapors from the distillation tank 58 to the tumbler/dryer 212. In this embodiment, the valve 62 is always partially open and acts as a throttling valve so that the pressure on the side of the valve 62 coupled to the distillation tank 58 is greater than the pressure on the other side of the valve 62.

While the hot vapors are being provided to the tumbler/dryer 212, the tumbler/dryer 212 is kept continuously at reduced pressure by drawing vapors therefrom using the pump 36 to pump vapors from the tumbler/dryer 212 through the valve 32 and the condenser 34. The resulting liquid solvent is provided from the pump 36 to the holding tank 38.

Accordingly, simultaneously throttling hot vapors from the distillation tank 58 to the clothes contained in the tumbler/dryer 212 while maintaining the pressure inside the tumbler/dryer 212 at a reduced level causes the solvent that is on the clothes to heat up and flash into a vapor which is then removed through the valve 32, the condenser 34, and the pump 36. Accordingly, the clothes are dried without introducing any solvent to the atmosphere or mixing any solvent with air. Instead, the solvent is removed from the clothes by introducing the hot solvent vapor and maintaining the reduced pressure in the tumbler/dryer 212, thus causing the solvent on the clothes to flash and be pumped out of the tumbler/dryer 212.

The system 200 of FIG. 3 also illustrates that the carbon filter 28 can be cleaned by the system 200 in a manner described below. The carbon filter 28 includes two activated carbon subfilters 220, 222 each having a respective heating element 224, 226. In practice, the carbon subfilters 220, 222 operate independently so that vapors to be filtered can be provided to the subfilter 220 via the valve 216 or can be provided to the subfilter 222 via the valve 214.

Gases from the subfilter 220 can be vented to the atmosphere via a valve 230. Similarly, gases from the sub filter 222 can be vented to the atmosphere via a valve 232. The output of the subfilter 220 can also be cycled into the system through a valve 234 which provides the output of the subfilter 220 to the condenser 34, the pump 36 and ultimately to the holding tank 38. Similarly, the output of the subfilter 222 can be cycled back into the system via a valve 236 which also provides the output to the condenser 34, the pump 36, and ultimately the holding tank 38. When the carbon contained in one of the carbon subfilters 220, 222 becomes saturated with contaminants, the system 200 can be used to strip the contaminants from the subfilters 220, 222. When one of the carbon subfilters 220, 222 is being stripped, the other one of the subfilters 220, 222 is used to filter the gaseous output in a manner described in more detail below.

The vapor output from the distillation tank 58 is connected via the throttling valve 62 to two valves 240, 242 which are respectively connected to the carbon subfilters 220, 222. The heated vapors from the distillation tank 58 can be further heated prior to reaching the carbon subfilters 220, 222 by using additional heaters 244, 246.

The carbon subfilter 220 is stripped using the following method. Initially, the carbon bed in the carbon subfilter 220 is heated using the heater 224. Then, a vacuum is drawn in the carbon subfilter 220 by opening the valve 234, and activating the pump 36. Following these steps, the heater 60 is activated by opening the valve 64 to provide steam from the steam source 18 to the heater 60, thus heating the solvent stored in the distillation tank 58. The solvent vapor is then provided through the valve 62 to the valve 240 and passes through the heater 244 to become superheated vapor that is provided to the carbon bed of the carbon sub filter 220. Simultaneously, a vacuum is maintained within the carbon sub filter 220 by opening the valve 234 and activating the pump 36. The superheated vapor provided to the carbon bed within the carbon subfilter 220 heats solvent that is embedded in liquid form within the carbon bed. The combination of heating the solvent and reducing the pressure maintained within the carbon subfilter 220 causes the liquid solvent embedded in the carbon to become a vapor which is then removed via the valve 234 and the pump 36.

Note that providing the condensed vapors to the holding tank 38 via the pump 36 may cause vapors to accumulate within the holding tank 38. While the carbon bed within the carbon subfilter 220 is being stripped, the additional vapors provided to the holding tank 38 are filtered via the carbon subfilter 222 by opening the valve 214 and venting the output of the carbon subfilter 222 to the atmosphere by opening the valve 232. Note also that the technique disclosed herein for stripping the carbon sub filters 220, 222 can be applied to other types of filters.

Referring to FIG. 4, a flow chart 250 illustrates the steps for stripping the carbon bed of the activated carbon sub filters 220, 222. At a first step 252 the heater for the carbon bed is activated. Following the step 252 is a step 254 where the solvent is heated as described above using the heater 60 to heat solvent in the distillation tank 58 and by using one of the heaters 244, 246.

Following the step 254 is a step 256 where the pressure about the carbon bed being stripped is reduced. Following the step 256 is a step 258 where the superheated vapor created at the step 254 is applied to the carbon bed. As discussed above, the reduced pressure is maintained in the carbon bed while the superheated vapor is applied thereto.

Although specific features of the invention are shown in some drawings and not others, this is for convenience only as each feature may be combined with any or all of the other features in accordance with the invention.

While the invention has been disclosed in connection with the preferred embodiments shown and described in detail, various modifications and improvements thereon will become readily apparent to those skilled in the art. Accordingly, the spirit and scope of the present invention is to be limited only by the following claims.

What is claimed is:

1. A method of stripping contaminants from a filter comprising the steps of:

subjecting the filter to a negative gauge pressure;

stripping contaminants from the filter by applying superheated solvent vapor to the filter while maintaining the negative gauge pressure, whereby the negative gauge pressure and the superheated solvent vapor combine to vaporize liquid contaminants embedded in the filter.

2. The method according to claim 1, further comprising the step of: heating the filter prior to subjecting the filter to the negative gauge pressure.

3. The method according to claim 1 wherein applying superheated vapor includes applying superheated vapor composed of a material being removed from the filter.

4. A method of stripping contaminants from an activated carbon filter, comprising the steps of:

subjecting the activated carbon filter to a negative gauge pressure;

stripping contaminants from the filter by applying superheated solvent vapor to the filter while maintaining the negative gauge pressure, whereby the negative gauge pressure and the superheated solvent vapor combine to vaporize liquid contaminants embedded in the filter.

5. The method according to claim 4, further including the step of: heating the filter prior to subjecting the filter to the negative gauge pressure.

6. The method according to claim 4, wherein applying superheated vapor includes applying superheated vapor composed of a material being removed from the filter.

* * * * *